United States Patent
Kang et al.

(10) Patent No.: US 10,653,872 B2
(45) Date of Patent: May 19, 2020

(54) ENERGY DELIVERY DEVICE FOR EXPANDING TUBULAR ORGAN

(71) Applicant: PUKYONG NATIONAL UNIVERSITY INDUSTRY-UNIVERSITY COOPERATION FOUNDATION, Busan (KR)

(72) Inventors: Hyun Wook Kang, Busan (KR); Hyoung Shin Lee, Busan (KR)

(73) Assignee: PUKYONG NATIONAL UNIVERSITY INDUSTRY-UNIVERSITY COOPERATION FOUNDATION, Busan (KR)

(*) Notice: Subject to any disclaimer, the term of this patent is extended or adjusted under 35 U.S.C. 154(b) by 422 days.

(21) Appl. No.: 15/408,247

(22) Filed: Jan. 17, 2017

(65) Prior Publication Data

US 2017/0209677 A1    Jul. 27, 2017

(30) Foreign Application Priority Data

Jan. 21, 2016   (KR) .................. 10-2016-0007571

(51) Int. Cl.
*A61B 18/22* (2006.01)
*A61M 29/00* (2006.01)
(Continued)

(52) U.S. Cl.
CPC .............. *A61M 29/00* (2013.01); *A61B 18/22* (2013.01); *A61N 5/0601* (2013.01);
(Continued)

(58) Field of Classification Search
CPC .......... A61B 18/00; A61B 2018/00053; A61B 2018/00184; A61B 2018/00196;
(Continued)

(56) References Cited

U.S. PATENT DOCUMENTS 7,074,233 B1 * 7/2006 Gowda .................. A61B 18/18
606/13
8,105,334 B2    1/2012 Cheng et al.
(Continued)

FOREIGN PATENT DOCUMENTS

| JP | 2002-541905 A | 12/2002 |
| KR | 10-2013-0027395 A | 3/2013 |
| WO | WO 00/62699 A2 | 10/2000 |

OTHER PUBLICATIONS

Jinhee Kwon et al., "Computational analysis of endometrial photocoagulation with diffusing optical device", Biomedical Optics Express, Oct. 14, 2013, pp. 2450-2462, vol. 4, No. 11, Optical Society of America.

*Primary Examiner* — Ahmed M Farah

(57) ABSTRACT

The present invention relates to an energy delivery device for expanding a tubular organ, the energy delivering device delivering energy to a tubular organ by an optical fiber for treatment and expanding a tissue in the tubular organ, the device comprising a light diffusing optical fiber connected between a laser device and a fixing tip and delivering light; a contraction unit having one end connected to the fixing tip and arranged in a circumference of an end of the light diffusing optical fiber; a movement unit closely adhered to the other end of the contraction unit, in which the light diffusing optical fiber is inserted; and an expansion adjustment unit adjusting a moving distance of the movement unit and expanding the contraction unit in a radial direction while contracting the contraction unit.

11 Claims, 5 Drawing Sheets

(51) Int. Cl.
*A61N 5/06* (2006.01)
*A61B 18/00* (2006.01)
*A61N 5/067* (2006.01)

(52) U.S. Cl.
CPC ............... *A61B 2018/00214* (2013.01); *A61B 2018/00267* (2013.01); *A61B 2018/00791* (2013.01); *A61M 2205/0266* (2013.01); *A61N 2005/063* (2013.01); *A61N 2005/067* (2013.01); *A61N 2005/0626* (2013.01)

(58) Field of Classification Search
CPC .. A61B 2018/00214; A61B 2018/0022; A61B 2018/00223; A61B 2018/00224; A61B 2018/00267; A61B 2018/00315; A61B 2018/00345; A61B 2018/00351; A61B 2018/00404; A61B 2018/0041; A61B 2018/00505; A61B 2018/00511; A61B 2018/00517; A61B 2018/00547; A61B 2018/00559; A61B 2018/00719; A61B 2018/00797; A61B 18/20; A61B 18/22; A61B 2018/225; A61B 2018/2253; A61B 2018/2255; A61B 2018/2261; A61B 18/24; A61B 18/245; A61B 18/26; A61N 5/06; A61N 5/0601; A61N 2005/0602; A61N 5/0603; A61N 2005/0626; A61N 2005/063; A61N 2005/067; A61M 2205/00; A61M 2205/02; A61M 2205/0266
USPC ............ 606/2, 2.5, 7, 13–19; 607/88–90, 92
See application file for complete search history.

(56) References Cited

U.S. PATENT DOCUMENTS

| | | |
|---|---|---|
| 2006/0271067 A1 | 10/2006 | Wolfe et al. |
| 2006/0259029 A1* | 11/2006 | Utley .................... A61B 18/12 606/41 |
| 2008/0119869 A1* | 5/2008 | Teague ................. A61B 17/221 606/127 |
| 2013/0253492 A1* | 9/2013 | Danek .................... A61B 18/08 606/21 |
| 2014/0114378 A1 | 4/2014 | Danek et al. |
| 2015/0157389 A1* | 6/2015 | Ben-Ezra ............... A61B 18/14 514/789 |

\* cited by examiner

ENERGY DELIVERY DEVICE FOR EXPANDING TUBULAR ORGAN

TECHNICAL FIELD

The present invention relates to an energy delivery device for expanding a tubular organ. More specifically, the present invention relates to an energy delivery device for expanding a tubular organ, arranging a contraction unit formed with a wire around a light diffusing optical fiber to induce change or treatment of a tissue in the tubular organ using the light diffusing optical fiber, and moving a movement unit closely adhered to the contraction unit to an expansion adjustment unit to expand the contraction unit in a radial direction, thereby maintaining a predetermined distance between the tissue of the tubular organ and a laser beam radiated through the light diffusing optical fiber.

BACKGROUND ART

The conventional therapies using optical fibers, which insert optical fibers into tubular body structures including bronchial tubes, blood vessels or ureters, i.e., tubular organs, to induce change or treatment of lesion tissues, deliver light only in a straightforward or lateral direction. In the field of laser therapy, a technique for allowing light delivery in multiple directions is required.

Further, in order to treat tubular organs, lumens of tubular organs are to be expanded. To this end, catheters or stents are conventionally used. However, there is a disadvantage that the permanent treatment is impossible with such catheters or stents.

In addition, it is important to center optical fibers in the tubular organs in order to achieve a consistent therapeutic effect and a constant temperature distribution upon treatment of lesion tissues in tubular organs using optical fibers. Also, a mechanical device is further required to uniformly induce the expansion of tubular organs with a constant force.

Moreover, it is necessary to obtain information on a temperature distribution and an expansion range in tubular organs upon treatment of lesion tissues in the tubular organs. Conventional therapies using optical fibers, however, do not provide such function.

SUMMARY OF INVENTION

The present invention is directed to resolve the problems above. It is an object of the present invention to provide an energy delivery device for expanding a tubular organ, arranging a contraction unit formed with a wire around the circumference of a light diffusing optical fiber inserted in the tubular organ, the contraction unit expanding in a radial direction around the circumference of the light diffusing optical fiber by a movement unit moved by an expansion adjustment unit, thereby maintaining a predetermined distance between the light diffusing optical fiber and the tissue in the tubular organ, to induce change or treatment of the tissue.

It is another object of the present invention to provide an energy delivery device for expanding a tubular organ, installing a temperature sensor and a pressure sensor in the contraction unit, thereby enabling to provide a temperature distribution and an expansion range of a tissue in a tubular organ in real time.

In order to achieve the above objects, an energy delivery device for expanding a tubular organ according to the present invention, the energy delivery device delivering energy to a tubular organ by an optical fiber for treatment and expanding a tissue in the tubular organ, includes a light diffusing optical fiber connected between a laser device and a fixing tip and delivering light; a contraction unit having one end connected to the fixing tip and arranged in a circumference of an end of the light diffusing optical fiber; a movement unit closely adhered to the other end of the contraction unit, into which the light diffusing optical fiber is inserted; and an expansion adjustment unit adjusting a moving distance of the movement unit and expanding the contraction unit in a radial direction while contracting the contraction unit.

Preferably, the light diffusing optical fiber forms a diffusion tip for the end connected to the fixing tip and further comprises a transparent protection tube surrounding the circumference of the diffusion tip. The transparent protection tube is preferably made of any one of silica, quartz, polyetheretherketone (PEEK), polycarbonate, polyethylene terephthalate (PET), perfluoroether (PFA), ethylene tetrafluoroethylene (ETFE), polyvinylidene fluoride (PVDF), or fluorinated ethylene propylene (FEP).

Preferably, the contraction unit is formed with a wire and has a cross section of a geometrical shape according to the number of at least three wires connected.

The wire is preferably coated with gold or silver.

Also, the wire is preferably made of a shape memory alloy.

Preferably, the metal wire is made of any one of nitinol (nickel and titanium alloy), titanium-palladium-nickel, nickel-titanium-copper, gold-cadmium, iron-zinc-copper-aluminum, titanium-niobium-aluminum, uranium-niobium, hafnium-titanium-nickel, iron-manganese-silicon, nickel-titanium, nickel-iron-zinc-aluminum, copper-aluminum-iron, titanium-niobium, zirconium-copper-zinc, nickel-zirconium-titanium, or stainless steel.

The wire is preferably made of a synthetic resin material selected from any one of polyetheretherketone (PEEK), polycarbonate, polyethylene terephthalate (PET), perfluoroether (PFA), ethylene tetrafluoroethylene (ETFE), polyvinylidene fluoride (PVDF), or fluorinated ethylene propylene (FEP).

The energy delivery device preferably further comprises a temperature sensor and a pressure sensor attached to an outer surface of the wire, respectively.

Preferably, the wire has a round or rectangular cross section.

Preferably, the movement unit is a tubular-shaped sheath, and the sheath is made of stainless steel.

The sheath is preferably fixed to the metal wire by a straight-line connection or a helical connection.

Also, the expansion adjustment unit preferably includes an adjuster closely adhered to an end of the movement unit on the opposite side of the contraction unit; an adjustment tube having the adjuster accommodated inside and connected, into which the movement unit and the light diffusing optical fiber are inserted; an adjustment knob connected to the adjuster and attached to a top outer surface of the adjustment tube; and a handle grip attached to a bottom outer surface of the adjustment tube.

The energy delivery device for expanding the tubular organ according to the present invention is capable of delivering light in multiple directions in a tubular organ tissue, thereby being greatly helpful for changing and treating a lesion tissue.

Also, the energy delivery device according to the present invention secures foundation that can apply the contraction unit in the circumference of the light diffusing optical fiber to various surgeries with an expansion therapy technique for a tubular organ using electromagnetic energy and shape memory alloy wire, and improves the availability of the contraction unit in the medical field.

In addition, the energy delivery device according to the present invention enables to provide a temperature distribution and an expansion range in a tissue of a tubular organ in real time by a temperature sensor and a pressure sensor, which is helpful for treatment.

In addition, the energy delivery device according to the present invention covers a variety of diseases and shortens a recovery period through safe and efficient laser diagnosis and therapy, thereby allowing more patients to reduce health-care costs in the long term through a one-time therapy.

DETAILED DESCRIPTION

Preferred embodiments of an energy delivery device for expanding a tubular organ according to the present invention will be described in detail with reference to the accompanying drawings. The present invention may be embodied in many different forms and should not be construed as limited to the embodiments set forth herein. The embodiments are provided by way of illustration only and so that the disclosure of the present invention will be thorough, complete and will fully convey the full scope of the invention to a person skilled in the art.

The present invention uses a light diffusing optical fiber to radiate light to an interior of a tubular organ and induce change and treatment of a tissue. Also, the present invention attaches a mechanical wire device as a contraction unit to an end of the light diffusing optical fiber to efficiently expand the tubular organ tissue and secure a distance for radiation, thereby maintaining a predetermined distance between the light diffusing optical fiber and the tissue and allowing a temperature sensor and a pressure sensor to measure a temperature distribution and a pressure distribution safely in the tubular organ.

In addition, the present invention uses expansion and contraction movement of a wire of the contraction unit to expand an interior of a tubular organ tissue. Here, the present invention uses a material with a high reflectivity, a high melting point, and a high tensile strength to form the contraction unit, which is a wire expansion device, thereby preventing a thermal impact that may occur when electromagnetic energy is radiated.

In addition, the present invention uses a light diffusing optical fiber to induce a constant temperature for treatment, while using low energy strength.

The constitution and function of the energy delivery device for expanding the tubular organ according to the present invention with the aforementioned features will be described in detail.

Figure 1:
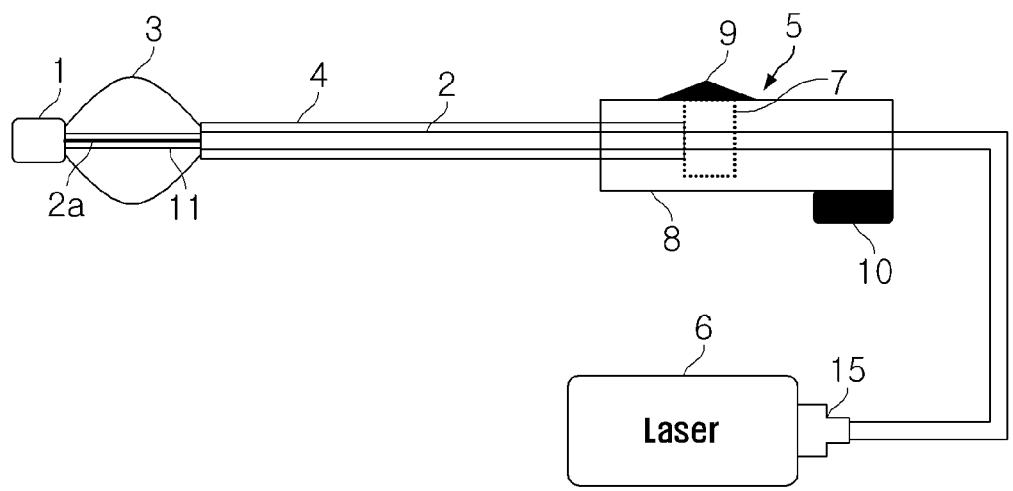
FIG. 1 is a schematic diagram illustrating an energy delivery device for expanding a tubular organ according to the present invention.

FIG. 1 is a schematic diagram illustrating an energy delivery device for expanding a tubular organ according to the present invention.

With reference to FIG. 1, the energy delivery device for expanding the tubular organ according to the present invention includes a fixing tip 1, a light diffusing optical fiber 2, a contraction unit 3, a movement unit 4, an expansion adjustment unit 5, and a laser device 6. The energy delivery device according to the present invention uses the light diffusing optical fiber 2 to radiate electromagnetic energy to a tissue of the tubular organ in all directions for treatment, and arranges a wire forming the contraction unit 3 in a circumference of a diffusion tip 2a of the light diffusing optical fiber 2 in order to help expanding an interior of the tubular organ tissue, thereby expanding the interior of the narrow tissue at once.

Specifically, the fixing tip 1 is attached to an end of the light diffusing optical fiber 2, and one side of a wire 3a forming the contraction unit 3 is connected to the inside of the fixing tip 1, and the other side of the wire 3a forming the contraction unit 3 is connected to an end of the movement unit 4 formed as a sheath. The light diffusing optical fiber 2 passes through the cavity of the sheath, movement unit 4, and has an end on the opposite side of the end attached to the fixing tip 1 connected to a laser device 6 by a connector 15. The other end of the sheath, movement unit 4, is connected to an expansion adjustment unit 5. Several strands of the wire 3a forming the contraction unit 3 are arranged along the outer circumference of the diffusion tip 2a of the light diffusing optical fiber 2 at a certain interval.

The end portion of the light diffusing optical fiber 2 connected to the fixing tip 1 is formed with the diffusion tip 2a diffusing light of a laser beam. In order to protect the optical fiber of the diffusion tip 2a from a mechanical impact, the diffusion tip 2a may be encompassed by a transparent protection tube 11 (spectral transmissivity>75%) made of any one of silica, quartz, polyetheretherketone (PEEK), polycarbonate, polyethylene terephthalate (PET), perfluoroether (PFA), ethylene tetrafluoroethylene (ETFE), polyvinylidene fluoride (PVDF), fluorinated ethylene propylene (FEP), etc. The light diffusing optical fiber 2 may be set to have a length ranging 1-20 mm.

The movement unit 4, a type of tubular sheath, moves forwards and backwards by the expansion adjustment unit 5 connected thereto, to contract the contraction unit 3 formed with the wire 3a in a longitudinal direction, thereby expanding the contraction unit 3 in a radial direction, or to return to the original shape.

The expansion adjustment unit 5 includes an adjuster 7, an adjustment tube 8, an adjustment knob and a handle grip 10. The adjuster 7 is closely adhered to an end of the movement unit 4, i.e., an end of the sheath, on the opposite side of the contraction unit 3. The end of the movement unit 4 and the light diffusing optical fiber 2 are inserted in and pass through the adjustment tube 8 having the adjuster 7 accommodated inside and connected. The adjustment knob 9 connected to the adjuster 7 is attached to a top outer surface of the adjustment tube 8, and the handle grip 10 is attached to an end of a bottom outer surface of the adjustment tube 8.

The energy delivery device for expanding the tubular organ according to the present invention delivers electromagnetic energy through a laser beam radiated by the laser device 6 and through the diffusion tip 2a of the light diffusing optical fiber 2 in a radial direction, in order to treat a lesion tissue in the tubular organ. The wavelength of the laser beam ranges 400-3000 nm, the output ranges 0.1-150 W, the time of radiation ranges 0.001-1000 ms, and the repetition rate of radiation ranges 1-100 Hz.

Figure 2A:
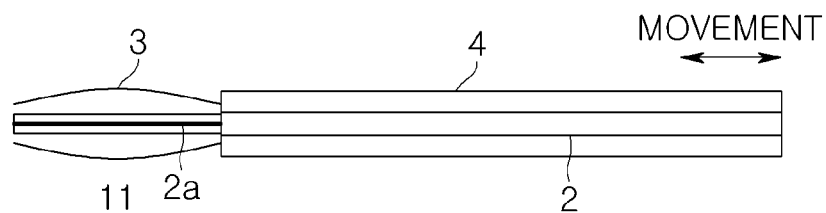
FIG. 2A and FIG. 2B are schematic diagrams illustrating an expansion of a contraction unit according to movement of a movement unit of an energy delivery device for expanding a tubular organ according to the present invention.
Figure 2B:
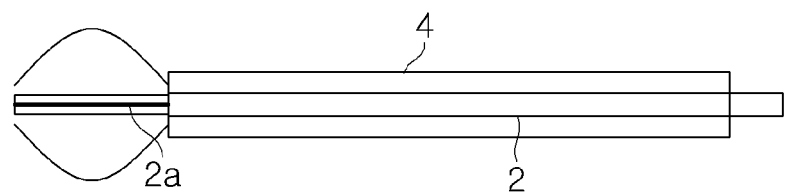

FIG. 2A and FIG. 2B are schematic diagram illustrating an expansion of the contraction unit according to movement of the movement unit of the energy delivery device for expanding the tubular organ according to the present invention.

With reference to FIG. 2, in order to obtain expansion and contraction movement of the wire 3a forming the contraction unit 3, the adjustment knob 9 is pushed or pulled with a finger while holding the handle grip 10 of the adjustment tube 8, to move the sheath, movement unit 4, forwards or backwards. Here, the moving distance is 0-50 mm. When the sheath, movement unit 4, which was in almost straight-line shape, as shown in FIG. 2A, moves forwards, the wire (3a) is contracted in a longitudinal direction to be pushed and expanded in a radial direction, and has a ball shape as shown in FIG. 2B. Thereby, a predetermined distance can be maintained between the wire and the circumference of the diffusion tip 2a of the light diffusing optical fiber 2.

The wire 3a of the contraction unit 3 is contracted to expand a lumen of a tubular organ tissue upon treatment of a lesion tissue. The interior of the tissue of the tubular organ expands in a radial direction along with the mechanical movement of the sheath, movement unit 4 so that the wire 3a forming the contraction unit 3 is contracted and expanded in a radial direction.

While the contradicted wire 3a expands in a radial direction and contacts an inner wall of the tubular organ tissue, the diffusion tip 2a of the light diffusing optical fiber 2 is centered in the lumen of the tubular organ tissue, and a predetermined distance is maintained between the diffusion tip 2a of the light diffusing optical fiber 2 and the tissue in the tubular organ. Thereby, electromagnetic energy per unit area can be uniformly radiated on the surface of the tissue.

The degree of expansion of the constitution unit 3 formed with the wire 3a may be determined by adjusting forward and backward movement of the adjuster 7 with the adjustment knob 9 connected to the adjuster 7 connected to the sheath, movement unit 4. While the sheath, movement unit 4, moves forwards or backwards, the wire 3a is contracted, and a distance from the diffusion tip 2a of the light diffusing optical fiber 2 to the contracted wire may be adjusted to 1-10 mm.

Figure 3A:
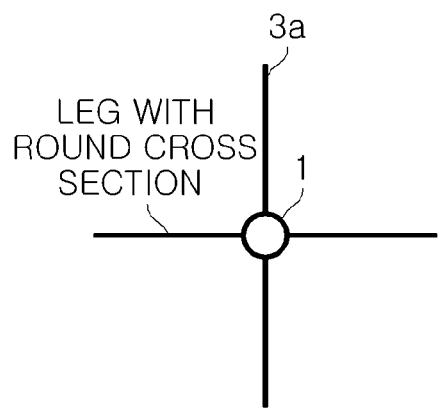
FIG. 3A and FIG. 3B are schematic diagrams illustrating a cross section of a wire forming a contraction unit of an energy delivery device for expanding a tubular organ according to the present invention.
Figure 3B:
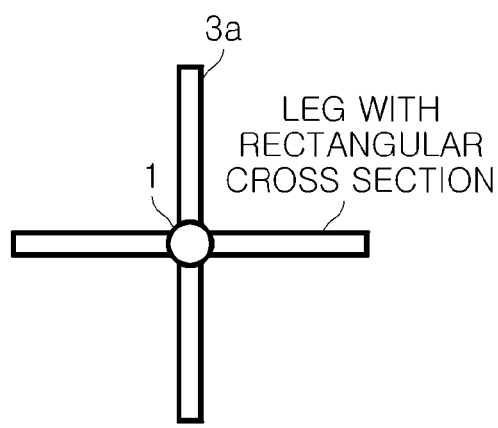

FIG. 3A and FIG. 3B are schematic diagrams illustrating a cross section of the wire forming the contraction unit of the energy delivery device for expanding the tubular organ according to the present invention.

With reference to FIG. 3A and FIG. 3B, the wire 3a forming the contraction unit 3 to be used for expanding a tubular organ tissue may have legs with a round cross section (FIG. 3A) or a rectangular cross section (FIG. 3A), with a thickness ranging 0.05-2 mm. In the case of the rectangular cross section, the wire 3a may have a width ranging 0.5-3 mm.

Figure 4A:
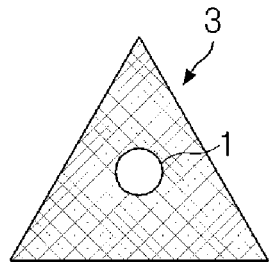
FIG. 4A, FIG. 4B and FIG. 4C are longitudinal-sectional views illustrating geometrical shapes of a contraction unit according to the number of wires of an energy delivery device for expanding a tubular organ according to the present invention.
Figure 4B:
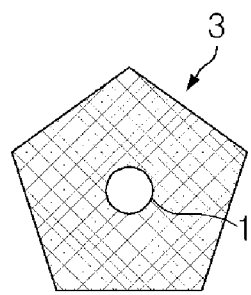
Figure 4C:
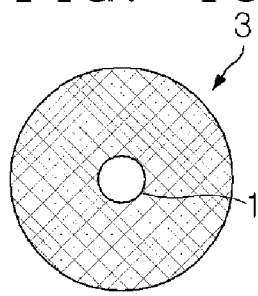

FIG. 4A, FIG. 4B and FIG. 4C are longitudinal-sectional views illustrating geometrical shapes of the contraction unit according to the number of wires of the energy delivery device for expanding the tubular organ according to the present invention.

With reference to FIG. 4A, FIG. 4B and FIG. 4C, at least three legs may be used for the wire 3a, several strands of which are arranged along the outer circumference of the diffusion tip 2a of the light diffusing optical fiber 2 at a certain interval, to form the contraction unit 3, according to the size of a tubular organ tissue to be treated and an anatomical element. The longitudinal section of the contraction unit 3 may have various geographical shapes, such as triangle (FIG. 4A) in the case of three legs, pentagon (FIG. 4B) in the case of five legs, circle (FIG. 4C) in the case of a plurality of legs, etc., according to the number of legs of the wire 3a.

Also, the wire 3a of the contraction unit 3 and the sheath, movement unit 4, may be connected and fixed by a straight-line connection or by a helical connection, such as screw connection, according to the size of a tubular organ tissue to be treated and an anatomical element.

A deformable shape memory alloy, etc. may be used for the wire 3a forming the contraction unit 3 to expand a tissue in a tubular organ. The material of the wire 3a made of metal including a shape memory alloy may include nitinol (nickel and titanium alloy), titanium-palladium-nickel, nickel-titanium-copper, gold-cadmium, iron-zinc-copper-aluminum, titanium-niobium-aluminum, uranium-niobium, hafnium-titanium-nickel, iron-manganese-silicon, nickel-titanium, nickel-iron-zinc-aluminum, copper-aluminum-iron, titanium-niobium, zirconium-copper-zinc, nickel-zirconium-titanium, stainless steel, etc.

A deformable synthetic resin material, etc. may be used for the wire 3a to expand a tissue. The synthetic resin material may include polyetheretherketone (PEEK), polycarbonate, polyethylene terephthalate (PET), perfluoroether (PFA), ethylene tetrafluoroethylene (ETFE), polyvinylidene fluoride (PVDF), fluorinated ethylene propylene (FEP), etc.

The electromagnetic energy may be radiated to the legs of the wire 3a forming the contraction unit 3 upon treatment of a tubular organ tissue by radiation of electromagnetic energy through a laser beam. In order to minimize a thermal impact by the radiation and at the same time minimize an energy absorption by the wire 3a, the material of the wire 3a preferably has a high reflexivity (>95% @ wavelength: 400-3000 nm) with respect to a wavelength radiated.

In order for the wire 3a constituting contraction unit 3 to have a high reflexivity upon radiation of electromagnetic energy, the material of the wire 3a may be coated with gold or silver. In addition, in order to minimize an increase in temperature at the wire 3a upon radiation of electromagnetic energy, an energy radiation method may be adjusted to a 15-75% duty cycle.

In order to minimize a thermal impact in the wire 3a forming the contraction unit 3 upon radiation of electromagnetic energy, the wire 3a may be made of a metal material having a high melting point (>500°) and a high tensile strength (>5 ksi). The material may include steel, gold or silver coating, titanium, tungsten, tungsten-rhenium alloy, superalloy (nickel, cobalt), niobium, tantalum, molybdenum, rhenium, etc. The sheath, movement unit 4, may be made of stainless steel.

Figure 5:
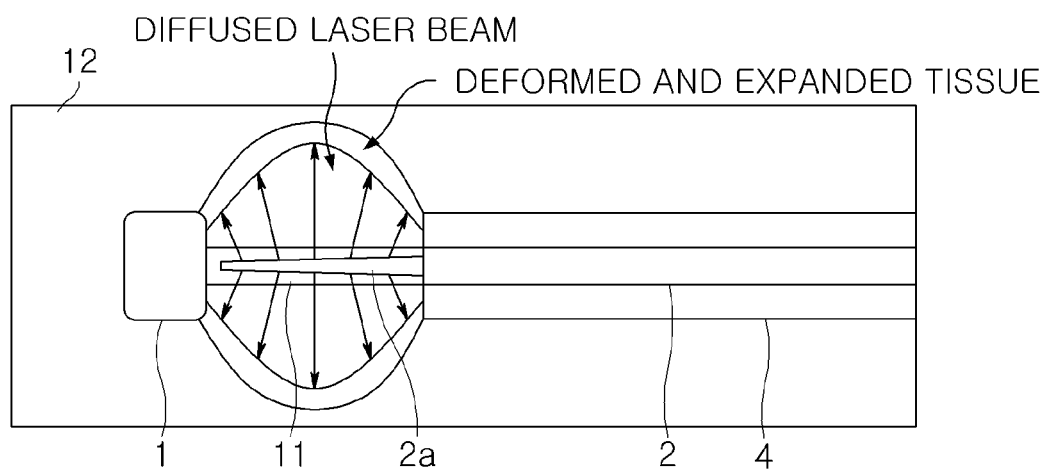
FIG. 5 is a schematic view illustrating an embodiment of treatment of a tubular organ tissue by an energy delivery device for expanding a tubular organ according to the present invention.

FIG. 5 is a schematic view illustrating an embodiment of treatment of a tubular organ tissue by the energy delivery device for expanding the tubular organ according to the present invention.

With reference to FIG. 5, in a treatment of a tubular organ tissue by the energy delivery device for expanding the tubular organ according to the present invention, the wire 3a forming the contraction unit 3 is contracted first to expand the interior of the tubular organ tissue 12, and electromagnetic energy of a laser beam is radiated by the laser device 6 and through the diffusion tip 2a of the light diffusing optical fiber 2 to cause deformation of the tissue 12 and induce treatment thereof. Tubular organs available for treatment may include bronchiole, bile duct, artery, vein, airway, pancreatic duct, ureter, urethra, GI duct, etc.

Figure 6:
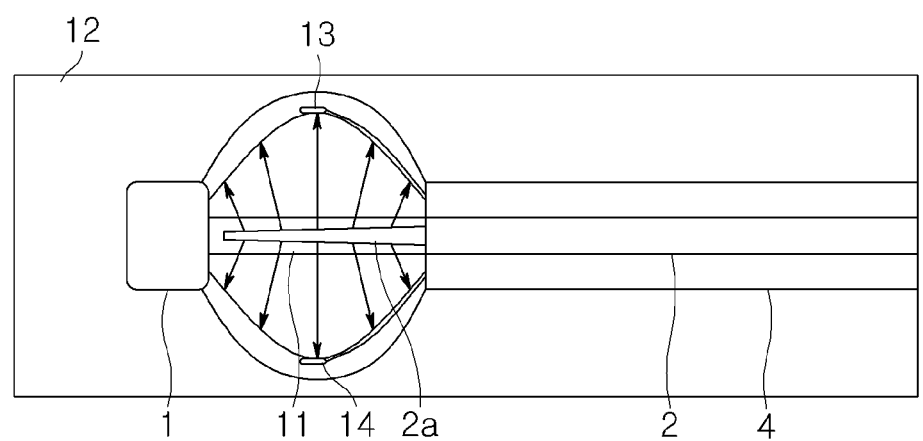
FIG. 6 is a schematic view illustrating an energy delivery device for expanding a tubular organ according to the present invention having a temperature sensor and a pressure sensor installed therein.

FIG. 6 is a schematic view illustrating the energy delivery device for expanding the tubular organ according to the present invention having a temperature sensor and a pressure sensor installed therein.

With reference to FIG. 6, in a treatment of a tissue of a tubular organ, a temperature sensor and a pressure sensor may be attached to a certain site on the outer circumferential surface of the wire 3a forming the contraction unit 3, in order to secure stability of treatment. The temperature sensor 13 is attached to the outer circumferential surface of the wire 3a and the pressure sensor 14 is attached to the outer circumferential surface on the opposite side of the temperature sensor, thereby providing information on a temperature and a pressure of the tubular organ tissue 12 in real time and monitoring the treatment procedure.

Figure 7:
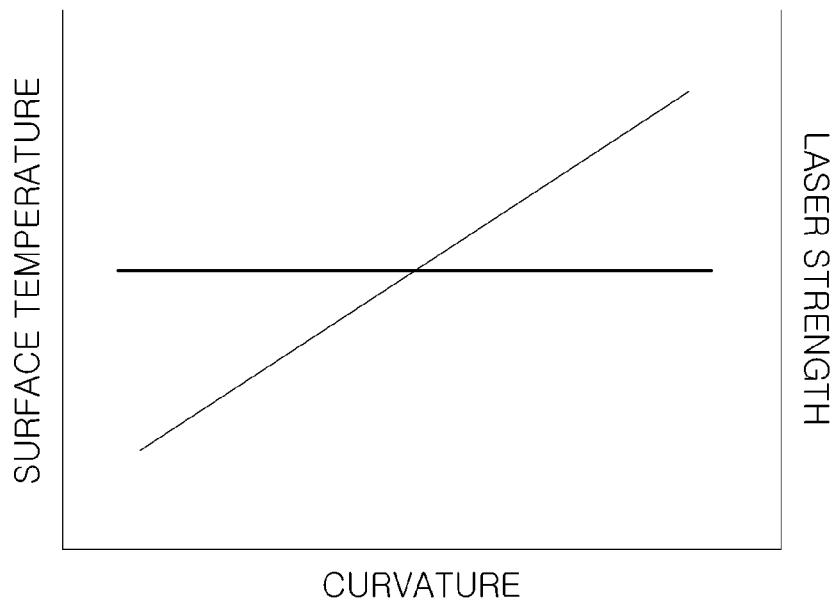
FIG. 7 is a graph illustrating constant temperature maintenance in a tissue through a change in electromagnetic energy according to a change in curvature upon treatment of a tubular organ tissue by an energy delivery device for expanding a tubular organ according to the present invention.
Figure 8:
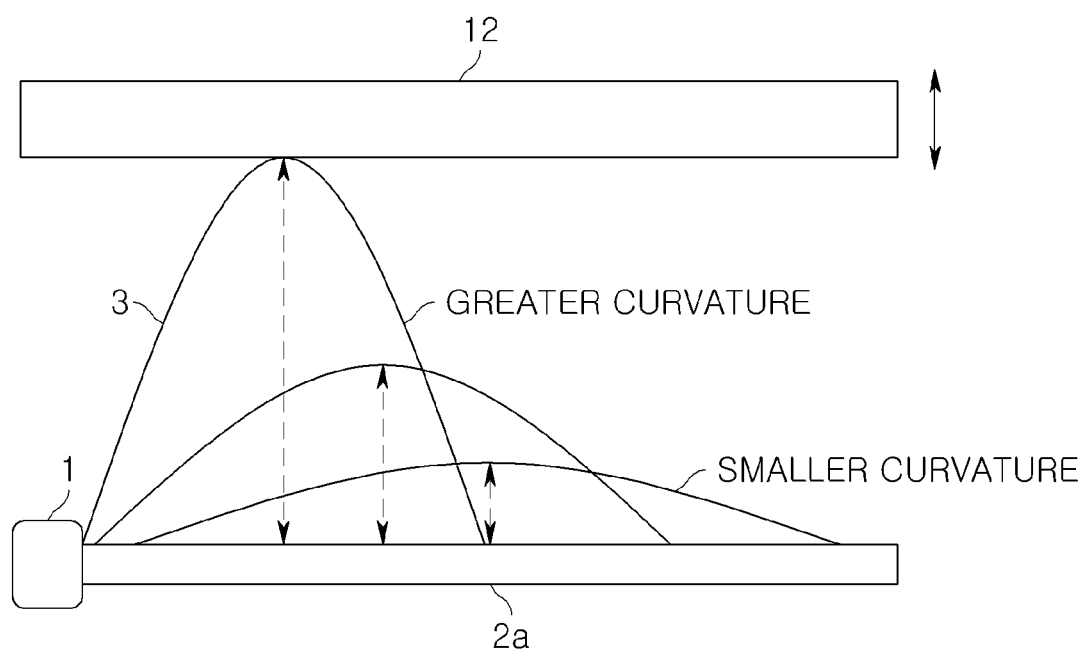
FIG. 8 is a diagram illustrating a change in curvature of a wire upon treatment of a tubular organ tissue by an energy delivery device for expanding a tubular organ according to the present invention.

FIG. 7 is a graph illustrating constant temperature maintenance in a tissue through a change in electromagnetic energy according to a change in curvature upon treatment of a tubular organ tissue by an energy delivery device for expanding a tubular organ according to the present invention. FIG. 8 is a diagram illustrating a change in curvature of a wire upon treatment of a tubular organ tissue by an energy delivery device for expanding a tubular organ according to the present invention.

With reference to FIG. 7 and FIG. 8, in order to maintain a temperature constantly upon treatment of a tubular organ tissue, the strength of electromagnetic energy is controlled simultaneously with or before the treatment according to the curvature of the wire (3a) contracted to keep an energy distribution per unit area uniformly, thereby enabling to maintain the temperature of the tubular organ tissue 12 for treatment at a constant treatment temperature (50-90°).

The energy delivery device for expanding the tubular organ according to the present invention is described with reference to the drawings. However, it should be construed that the present invention is not limited to the embodiments and drawings disclosed herein and may be embodied in various modifications by a person skilled in the art without departing from the spirit of the present invention.

What is claimed is:

1. An energy delivery device for delivering energy to a tubular organ by an optical fiber for treatment and expanding a tissue in the tubular organ, comprising:
    a light diffusing optical fiber connected between a laser device and a fixing tip and delivering light;
    a contraction unit having one end connected to the fixing tip and arranged in a circumference of an end of the light diffusing optical fiber, wherein the end of the light diffusing optical fiber is formed with a diffusion tip;
    a transparent protection tube surrounding the circumference of the diffusion tip;
    a movement unit closely adhered to the other end of the contraction unit, into which the light diffusing optical fiber is inserted; and
    an expansion adjustment unit adjusting a moving distance of the movement unit and expanding the contraction unit in a radial direction while longitudinally contracting the contraction unit,
    wherein the expansion adjustment unit comprises:
        an adjuster closely adhered to an end of the movement unit on the opposite side of the contraction unit;
        an adjustment tube having the adjuster accommodated inside and connected to an adjustment knob;
        the adjustment knob connected to the adjuster and attached to a top outer surface of the adjustment tube; and
        a handle grip attached to a bottom outer surface of the adjustment tube.

2. The energy delivery device of claim 1, wherein the transparent protection tube is made of any one of silica, quartz, polyetheretherketone (PEEK), polycarbonate, polyethylene terephthalate (PET), perfluoroether (PFA), ethylene tetrafluoroethylene (ETFE), polyvinylidene fluoride (PVDF), or fluorinated ethylene propylene (FEP).

3. The energy delivery device of claim 1, wherein the contraction unit is formed with a wire.

4. The energy delivery device of claim 3, wherein the contraction unit has a cross section of a geometrical shape according to three or more wires connected to the fixing tip.

5. The energy delivery device of claim 3, wherein the wire is a metal wire made of a shape memory alloy.

6. The energy delivery device of claim 5, wherein the metal wire is made of any one of nitinol (nickel and titanium alloy), titanium-palladium-nickel, nickel-titanium-copper, gold-cadmium, iron-zinc-copper-aluminum, titanium-niobium-aluminum, uranium-niobium, hafnium-titanium-nickel, iron-manganese-silicon, nickel-titanium, nickel-iron-zinc-aluminum, copper-aluminum-iron, titanium-niobium, zirconium-copper-zinc, nickel-zirconium-titanium, or stainless steel.

7. The energy delivery device of claim 3, further comprising a temperature sensor and a pressure sensor attached to an outer surface of the wire, respectively.

8. The energy delivery device of claim 3, wherein the wire has a round or rectangular cross section.

9. The energy delivery device of claim 3, wherein the movement unit is a tubular-shaped sheath.

10. The energy delivery device of claim 9, wherein the sheath is made of stainless steel.

11. The energy delivery device of claim 9, wherein the sheath is fixed to the metal wire by a straight-line connection or a helical connection.

* * * * *